(12) United States Patent
Hannafin et al.

(10) Patent No.: US 11,279,075 B2
(45) Date of Patent: Mar. 22, 2022

(54) SYSTEM AND METHOD FOR STERILIZATION OF MEDICAL INSTRUMENTS WITHIN A HYDROGEN PEROXIDE STERILIZATION PROCESS

(71) Applicant: Symmetry Medical Manufacturing, Inc., Warsaw, IN (US)

(72) Inventors: George P. Hannafin, Hudson, NH (US); Jason Hawkes, Weare, NH (US)

(73) Assignee: SYMMETRY MEDICAL MANUFACTURING, INC., Warsaw, IN (US)

( * ) Notice: Subject to any disclaimer, the term of this patent is extended or adjusted under 35 U.S.C. 154(b) by 148 days.

(21) Appl. No.: 15/874,230

(22) Filed: Jan. 18, 2018

(65) Prior Publication Data

US 2018/0141262 A1    May 24, 2018

Related U.S. Application Data

(62) Division of application No. 15/080,992, filed on Mar. 25, 2016, now abandoned.

(60) Provisional application No. 62/166,994, filed on May 27, 2015, provisional application No. 62/149,032, filed on Apr. 17, 2015.

(51) Int. Cl.
| | |
|---|---|
| *B29C 51/02* | (2006.01) |
| *A61L 2/07* | (2006.01) |
| *A61L 2/20* | (2006.01) |
| *B29L 31/00* | (2006.01) |
| *B29K 23/00* | (2006.01) |
| *B29K 309/08* | (2006.01) |

(52) U.S. Cl.
CPC ............. *B29C 51/02* (2013.01); *A61L 2/07* (2013.01); *A61L 2/206* (2013.01); *A61L 2/208* (2013.01); *B29K 2023/12* (2013.01); *B29K 2309/08* (2013.01); *B29L 2031/7162* (2013.01)

(58) Field of Classification Search
CPC ..................................................... B29C 51/02
USPC ........................................................ 422/27
See application file for complete search history.

(56) References Cited

U.S. PATENT DOCUMENTS

| | | | |
|---|---|---|---|
| 4,568,529 | A | 2/1986 | Leconte |
| 4,797,438 | A | 1/1989 | Kletecka et al. |
| 5,286,776 | A | 2/1994 | Ichikawa et al. |
| 5,628,970 | A | 5/1997 | Basile et al. |
| 6,015,529 | A | 1/2000 | Lin et al. |
| 6,248,293 | B1 | 6/2001 | Davis et al. |
| 6,692,693 | B2 | 2/2004 | Wu |
| 7,834,089 | B2 | 11/2010 | Zhang |
| 2002/0192108 | A1 | 12/2002 | Wu |
| 2011/0240064 | A1 | 10/2011 | Wales et al. |

(Continued)

OTHER PUBLICATIONS

Rosato et al., Plastics Design Handbook, 2001, Springer Science+Business Media (Year: 2001).*

(Continued)

*Primary Examiner* — Holly Kipouros
(74) *Attorney, Agent, or Firm* — Hayes Soloway PC

(57) ABSTRACT

A system and method of sterilization for medical instruments within a hydrogen peroxide sterilization process is provided. A medical instrument is housed in a sterilization tray, wherein the sterilization tray is formed from polypropylene and a glass material. The medical instrument and sterilization tray are subjected to a hydrogen peroxide sterilant.

4 Claims, 3 Drawing Sheets

(56) References Cited

U.S. PATENT DOCUMENTS

2017/0029611 A1   2/2017   Amano

OTHER PUBLICATIONS

Yalcin; "3M Glass Bubbles iM16K for Reinforced Thermoplastics"; Benefits of Hollow Glass Microspheres in Glass Fiber Reinforced Thermoplastics; 2013; p. 1-5; 3M.

* cited by examiner

SYSTEM AND METHOD FOR STERILIZATION OF MEDICAL INSTRUMENTS WITHIN A HYDROGEN PEROXIDE STERILIZATION PROCESS

CROSS REFERENCE TO RELATED APPLICATION

This application is a divisional of U.S. patent application Ser. No. 15/080,992, entitled, "System and Method for Sterilization of Medical Instruments within a Hydrogen Peroxide Sterilization Process" filed Mar. 25, 2016, which itself claims benefit of U.S. Provisional Application Ser. No. 62/149,032, entitled, "System and Method for Sterilization of Medical Instruments Within a Hydrogen Peroxide Sterilization Process" filed Apr. 17, 2015 and U.S. Provisional Application Ser. No. 62/166,994, entitled, "System and Method for Sterilization of Medical Instruments Within a Hydrogen Peroxide Sterilization Process" filed May 27, 2015, the entire disclosure of which is incorporated herein by reference.

FIELD OF THE DISCLOSURE

The present disclosure is generally related to sterilization of medical instruments and more particularly is related to a system and method for sterilization of medical instruments within a hydrogen peroxide sterilization process.

BACKGROUND OF THE DISCLOSURE

The sterilization of medical instruments and tools before, after, and sometimes during medical procedures is a foundation of modern health care, as it is imperative in preventing the spread of harmful contaminants. Commonly, medical instruments are held within sterilization trays which are then processed through a sterilization operation. The sterilization operation can include sterilization within an autoclave, which is a pressure chamber that subjects the medical instruments to high pressure saturated steam at approximately 250° F.-270° F. for a period of time. Other sterilization processes include the use of chemical sterilant or light-based sterilizing devices.

Sterilization trays used within the medical industry are commonly manufactured from polyphenylsulfone (PPSU) often known by the brand name RADEL®. The PPSU utilizes an extrusion process combined with a thermoforming process or is injection molded from resin. These PPSU have proven successful in many types of sterilization processes, such as within the steam autoclave, but they have points of failure in low temperature sterilization processes. For example, low-temperature chemical sterilizing using hydrogen peroxide has become more commonplace when sterilizing medical instruments that cannot tolerate steam sterilization. When the PPSU is subjected to hydrogen peroxide sterilization, however, the hydrogen peroxide is absorbed and causes the PPSU to discolor and become brittle over time, which leads to tray failure, or worse, ineffective sterilization due to a drop in the concentration level of hydrogen peroxide in the sterilization chamber.

Thus, a heretofore unaddressed need exists in the industry to address the aforementioned deficiencies and inadequacies.

SUMMARY OF THE DISCLOSURE

Embodiments of the present disclosure provide a system and method for sterilization of medical instruments within a hydrogen peroxide sterilization process. Briefly described, in architecture, one embodiment of the method, among others, can be broadly summarized by the following steps: housing a medical instrument on a sterilization tray, wherein the sterilization tray is formed from polypropylene and a glass material; and subjecting the medical instrument and sterilization tray to a hydrogen peroxide sterilant. The sterilization tray may be formed from polypropylene and the glass material by first injection molding the polypropylene and the glass material into a sheet form and then thermoforming the sheet form of the polypropylene and the glass material into a tray form. In one of many alternatives, the sterilization tray may be formed from polypropylene and the glass material by injection molding the polypropylene and the glass material into a tray form.

The present disclosure can also be viewed as providing methods of manufacturing and using a sterilization tray. In this regard, one embodiment of such a method, among others, can be broadly summarized by the following steps: combining a quantity of polypropylene with a glass material; injecting the combined quantity of polypropylene with glass material into a sheet form; thermoforming the sheet form of the combined quantity of polypropylene with glass material into a tray form, thereby providing a sterilization tray; and subjecting the sterilization tray to a hydrogen peroxide sterilant.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
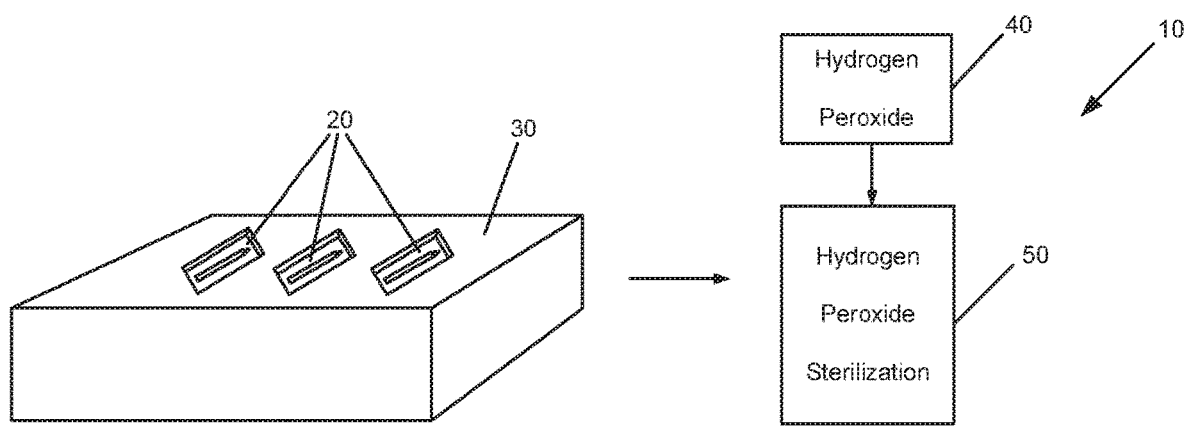
FIG. 1 is a schematic illustration of a method of sterilizing medical instruments within a hydrogen peroxide sterilization process, in accordance with a first exemplary embodiment of the present disclosure.

FIG. 1 is a schematic illustration of a method of sterilizing medical instruments within a hydrogen peroxide sterilization process 10, in accordance with a first exemplary embodiment of the present disclosure. The method of sterilizing medical instruments within a hydrogen peroxide sterilization process 10, which may be referred to herein simply as 'method 10' includes housing a medical instrument 20 in a sterilization tray 30, wherein the sterilization tray is formed from polypropylene and a glass material. The medical instrument 20 and sterilization tray 30 are subjected to a hydrogen peroxide sterilant 40 within a hydrogen peroxide sterilization process 50.

Unlike a hydrogen peroxide sterilization process used with conventional PPSU sterilization trays, which are prone to degrading after being subjected to hydrogen peroxide, it has been found that trays formed from polypropylene (PP) and a glass material, such as glass fibers, glass spheres, or a combination thereof, can prove to be successful in hydrogen peroxide sterilization. The combination of PP and the glass material resists penetration of the hydrogen peroxide into the surface of the tray, since the PP and glass material provide for a less porous surface than conventional PPSU and glass trays. Thus, while PPSU absorbs hydrogen peroxide in low-temperature, PP with glass does not. Accordingly, PP and glass material formed trays may be capable of long term, successful use with hydrogen peroxide sterilization. Further, the process described herein may, in some situations, be used with ethylene oxide or other chemical sterilants.

Figure 2:
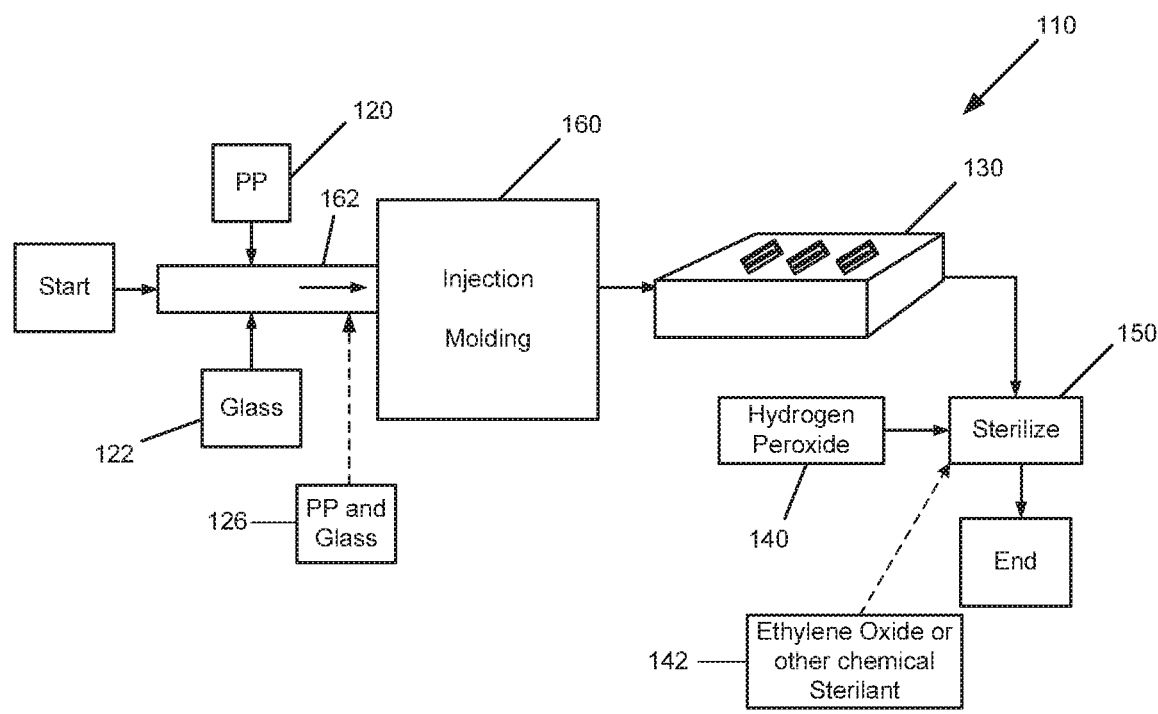
FIG. 2 is a schematic illustration of a method of manufacturing and using a sterilization tray, in accordance with a second exemplary embodiment of the present disclosure.

FIG. 2 is a schematic illustration of a method of manufacturing and using a sterilization tray 110, in accordance with a second exemplary embodiment of the present disclosure. The method of manufacturing and using a sterilization tray 110, which may be referred to herein simply as 'method 110'' includes forming the medical sterilization tray 130 by injection molding a polypropylene (PP) 120 and a glass material 122 into a tray form. The PP 120 and the glass material 122 may be provided to an inlet 162 of an injection molding device 160. The PP 120 and glass material 122 may be pre-mixed into a resin 126, without the addition of copolymers, prior to being fed into the inlet 162 of the injection molding device 160. Inside the injection molding device 160, the combined resin may be injected into a mold having a tray-form shape, which may include any type of shape to house medical instruments. The resulting tray 130 may then be used to sterilize medical instruments within a low-temperature hydrogen peroxide sterilization device 150. The sterilization device 150 receives an input of hydrogen peroxide 140 which is applied to the tray 130 and the medical instruments thereon, and effectively sterilizes the instruments, as is known in the art. Alternatively, or in addition, the sterilization device 150 may receive an input of steam 144 for use in sterilization, and/or the sterilization device may receive an input of a chemical sterilant including, but not limited to an ethylene-oxide based sterilant 142.

In comparison to PPSU which is commonly used in medical sterilization trays, PP has a higher melt flow rate than PPSU and therefore PP is often more successfully used in injection molding. It is noted that the glass material 122 may include a variety of types of glass fillers and other materials. Commonly, glass fibers, glass spheres, or a combination of glass fibers and spheres may be used with the PP. The glass filling material 122 may provide rigidity to the eventual tray 130, such that it can support medical instruments properly. Up to 30% of the sterilization tray material may be glass fiber and/or glass spheres. While other materials and fillers may be included, the use of EVAL®, EVOH resin and film (ethylene vinyl alcohol copolymer) may be restricted or fully omitted from the combined resin and the resulting tray 130.

Figure 3:
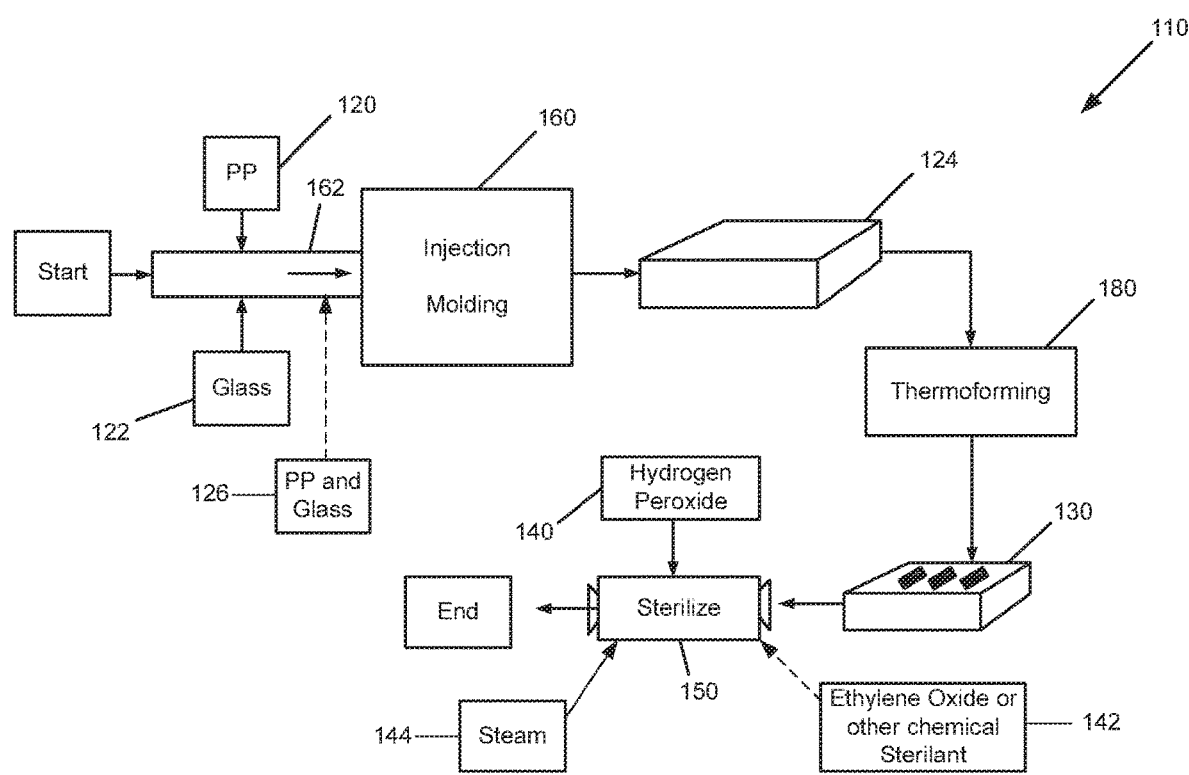
FIG. 3 is a schematic illustration of a method of manufacturing and using a sterilization tray, in accordance with the second exemplary embodiment of the present disclosure.

FIG. 3 is a schematic illustration of a method of manufacturing and using a sterilization tray 110, in accordance with the second exemplary embodiment of the present disclosure. Similar to FIG. 2, the method 110 includes forming the medical sterilization tray 130 by injection molding a PP 120 and a glass material 122. However, the method of FIG. 3 includes further injection molding the PP 120 and the glass material 122 into a sheet form 124, first, and then thermoforming the sheet form 124 of the PP 120 and the glass material 122 into a tray form.

In this process, the PP 120 and the glass material 122 may be provided to an inlet 162 of an injection molding device 160. The PP 120 and glass material 122 may be pre-mixed into a resin, without the addition of copolymers, prior to being fed into the inlet 162 of the injection molding device 160. Inside the injection molding device 160, the combined resin may be injected into a mold having a sheet form, e.g., a substantially planar sheet that is sized for thermoforming. Once cooled fully, the sheet form of the combined resin may be placed in a thermoforming device 180. Within the thermoforming device 180, the sheet form of the combined resin is heated to a pliable forming temperature and formed to a tray-shape in a mold, which may include any type of shape to house medical instruments. The tray-shape is trimmed to create a final medical sterilization tray 130, which may then be used to sterilize medical instruments within a low-temperature hydrogen peroxide sterilization device 150. The sterilization device 150 receives an input of hydrogen peroxide 140 which is applied to the tray 130 and the medical instruments thereon, and effectively sterilizes the instruments, as is known in the art.

It has been found that thermoforming PP materials alone may result in non-usable products, since the PP is often incapable of withstanding the thermoforming process. The glass filling materials 122 may be used to properly thermoform the sheet-form of the combined resin by helping the sheet-form of the combined resin maintain uniformity in shape. In one example, it has been found that the combined use of glass fibers and glass spheres may provide substantial benefits in maintaining uniformity during the cool down process after thermoforming.

It should be noted that any process descriptions or blocks in flow charts should be understood as representing modules, segments, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A method of manufacturing and using a sterilization tray comprising:

combining a quantity of polypropylene with a glass material comprising glass spheres and glass fibers;

injecting the combined quantity of polypropylene with glass material into a sheet form;

premixing the polypropylene and the glass material into a resin without the addition of copolymers prior to the injection molding;

thermoforming the sheet form of the combined quantity of polypropylene with glass material into a tray form, wherein the tray form defines at least one recess for housing at least one medical instrument for sterilization, thereby providing a sterilization tray; and subjecting the sterilization tray to a hydrogen peroxide sterilant.

2. The method of claim 1, wherein the sterilization tray includes up to 30% glass material.

3. The method of claim 1, further comprising:

subjecting the medical instrument and sterilization tray to a steam sterilization.

4. The method of claim 1, further comprising the step of subjecting the sterilization tray to an ethylene oxide sterilant.

\* \* \* \* \*